United States Patent [19]
Aubrey

[11] Patent Number: 5,328,398
[45] Date of Patent: Jul. 12, 1994

[54] WATER SKI VEST HAVING AN INTEGRAL LUMBAR COMPRESSION BELT

[76] Inventor: Martin G. Aubrey, 100 McWaine La., Cary, N.C. 27513

[21] Appl. No.: 145,153

[22] Filed: Nov. 3, 1993

[51] Int. Cl.$^5$ .............................................. B63C 9/08
[52] U.S. Cl. .................................... 441/106; 441/108
[58] Field of Search ............... 441/106, 107, 108, 112, 441/113, , 114, 115, 117, 118, 125; 128/78; 2/2.5, 2.1 R, 44

[56] References Cited
U.S. PATENT DOCUMENTS

| | | |
|---|---|---|
| 4,175,553 | 11/1979 | Rosenberg ................................ 2/44 |
| 4,820,221 | 4/1989 | Aubrey ................................ 441/106 |
| 4,936,805 | 6/1990 | Piat, Jr. ................................ 441/106 |

Primary Examiner—Jesus D. Sotelo
Attorney, Agent, or Firm—Rhodes, Coats & Bennett

[57] ABSTRACT

The present invention entails a water ski vest having an integral lumbar compression belt. A lumbar compression belt is secured to the inside back of the ski vest and the compression belt includes a lower portion that covers and wraps around the lumbar region of the subject or person wearing the water ski vest. By first fastening the compression belt the lumbar region of the person is compressed and positively supported. Thereafter, additional support is provided by fastening the water ski vest about the lumbar compression belt.

8 Claims, 2 Drawing Sheets

WATER SKI VEST HAVING AN INTEGRAL LUMBAR COMPRESSION BELT

FIELD OF INVENTION

The present invention relates to buoyant water ski garments and more particularly to buoyant upper body garments that are provided with integral positive lumbar support.

BACKGROUND OF THE INVENTION

It has been known to provide positive lumbar support in a water ski vest. For example, in my U.S. Pat. No. 4,820,221, I disclosed a water ski vest having a relatively hard frame structure implanted into the vest. This frame extended down the back of the water ski vest and extended over the lumbar region of the subject's lower back. Consequently, the water ski vest disclosed in U.S. Pat. No. 4,820,221, provided positive lumbar support for the subject wearing the vest.

However, the design of the lumbar support structure shown in U.S. Pat. No. 4,820,221, basically lent itself to custom applications. That is, this design is best suited to a situation where the inner lumbar support frame is custom designed to fit the individuals back. Thus, the water ski-lumbar support structure of U.S. Pat. No. 4,820,221 is not particularly suited for mass merchandising.

After the advent of the water ski vest shown in U.S. Pat. No. 4,820,221, there has been additional work in the area of improving back support in water ski vests. For example, U.S. Pat. No. 4,936,805 addressed the problem of providing additional back support structure in a water ski vest. A review of this patent shows the use of a belt and plastic plate structure in conjunction with the water ski vest. In particular, the belt is designed to simply hold the plastic plate against the small of the back for providing additional back support structure to the person wearing the water ski vest. Despite the references to the lumbar region, the design of the water ski vest shown in U.S. Pat. No. 4,936,805 is such that the plastic plate only controls and provides support to the small of the back and not to the lumbar region.

Therefore, there has been and continues to be a need for a water ski vest that is comfortable, easy to use, and which provides direct and positive lumbar support to the person wearing the ski vest.

SUMMARY AND OBJECTS OF THE INVENTION

The present invention entails a water ski vest having a lumbar compression belt integrally formed therewith. The lumbar compression belt is disposed about the lower inside of the water ski vest and is designed to be wrapped and fastened around the wearer in such a fashion that the compression belt extends over and around the lumbar region of the subject and imparts positive lumbar support to that area.

It is therefore an object of the present invention to provide a buoyant upper body garment that provides positive lumbar support to an individual wearing the garment.

Another object of the present invention resides in the provision of a buoyant upper body garment that is provided with positive lumbar support and which does not require custom fitting but would be adaptable for use with a range of individuals of different sizes.

A further object of the present invention resides in the provision of a water ski vest having an integral compression belt secured to the inside thereof wherein the water ski vest and compression belt are adapted to be secured around the individual wearing the ski vest such that the compression belt extends downwardly and wraps around the lumbar region of the subject such that the compression belt imparts positive lumbar support to the subject.

A further object of the present invention resides in the provision of a water ski vest of the character referred to above that is designed to impart comfort to the user.

Another object of the present invention resides in the provision of a water ski vest with positive lumbar support that is easy to use and which can be conveniently fitted and fastened around an individual.

Other objects and advantages of the present invention will become apparent and obvious from a study of the following description and the accompanying drawings which are merely illustrative of such invention.

DETAILED DESCRIPTION OF THE INVENTION

Figure 1:
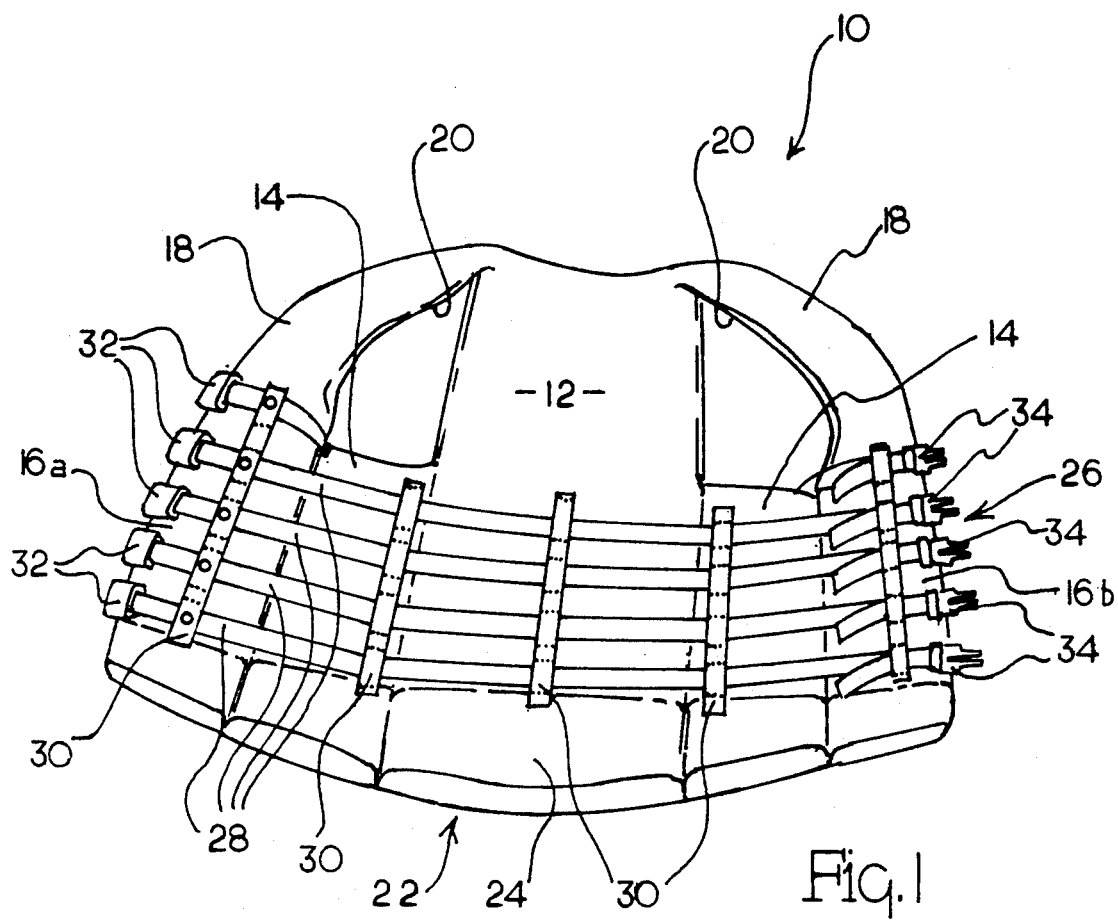
FIG. 1 is a plan view of the water ski vest of the present invention disposed in an open position and viewed from the exterior thereof.

With further reference to the drawings, the water ski vest having the positive lumbar support incorporated therein is shown in the drawings and indicated generally by the numeral 10. Viewing the water ski vest 10 in more detail, it is seen that the same includes a back panel 12 and when disposed and fitted about a person includes opposed sides 14 and an openable front indicated generally by the numeral 16, with the front being comprised of two front panels 16a and 16b. Extending from the upper outer edges of the back panel 12 is a pair of shoulder panels 18 that extend downwardly and join the front panels 16a and 16b. It is seen in the drawings that the shoulder panels 18 along with the back 12, sides 14 and front panels 16a and 16b, form a pair of arm openings 20.

Water ski vest 10 of the present invention is extended downwardly to cover and support the lumbar region LR of a person wearing the ski vest. In particular, the ski vest is provided with a lumbar extension indicated generally by the numeral 22. The lumbar extension 22 joins the lower edge of the ski vest 10 and extends a selected distance downwardly therefrom. As particularly illustrated in FIG. 1, the lumbar extension 22 includes a central lumbar extension panel 24 that extends downwardly from the back panel 12. It is appreciated from viewing FIG. 1 that the lumbar extension 22 has its greatest depth or height directly below the back panel 12. On opposite sides of the central lumbar extension panel 24, the lumbar extension 22 tends to curve and move upwardly around the sides 14 and the front panels 16a and 16b. Consequently, it is appreciated that the water ski vest 10 with the lumbar extension 22 has its greatest depth or height along the back central area. This is because the water ski vest 10 is deliberately extended such that it covers and wraps around the lumbar region LR of the individual person wearing the water ski vest 10.

Water ski vest 10 includes a fastener assembly indicated generally by the numeral 26 that is designed to effectively secure the front panels 16a and 16b close together and around a person wearing the vest. Viewing the fastener assembly 26 in more detail, it is seen that the same includes a series of elongated belts 28 that extend generally horizontally around the exterior surface of the water ski vest 10. To maintain the belts 28 in an appropriate spacing, there is provided a series of vertical guides 30 secured around the ski vest 10 and including through openings for permitting belts 28 to be threaded therethrough. Disposed on opposite ends of each belt 28 is a female receptor 32 and a male connector 34. Details of the fastener assembly 26 are not dealt with herein because such fasteners are well-known in the water ski vest art and are not per se material to the present invention.

Figure 2:
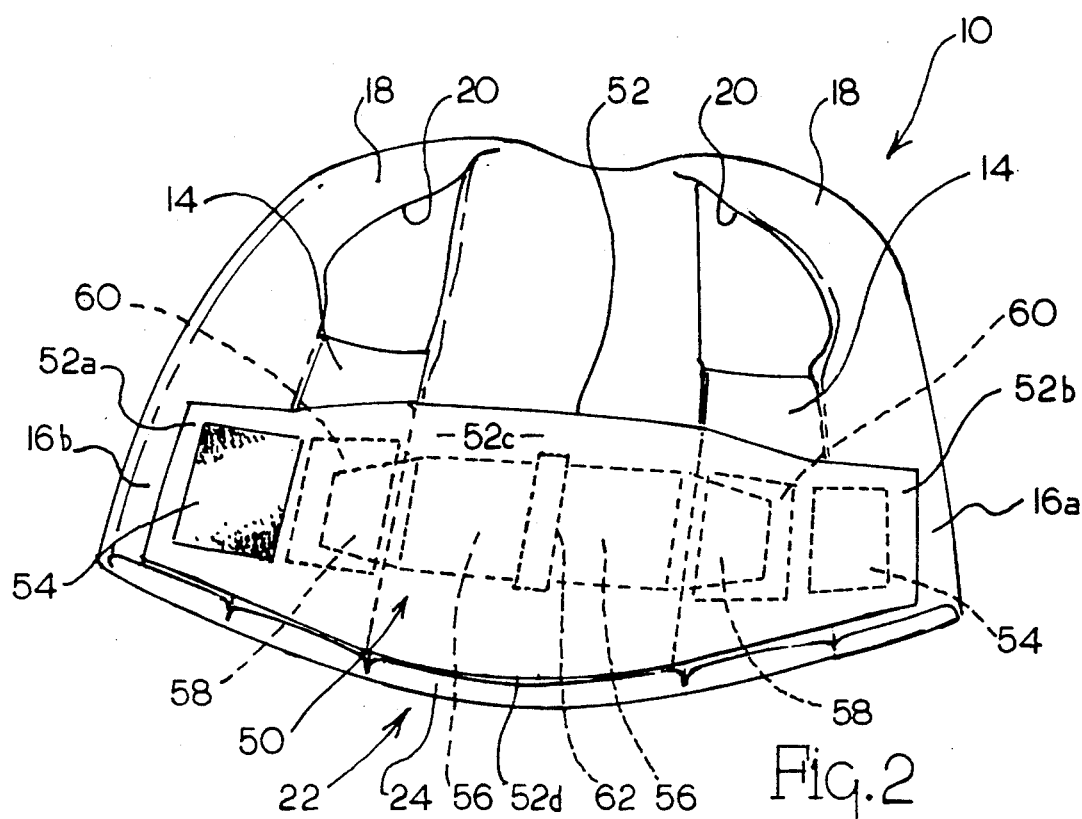
FIG. 2 is a plan view of the water ski vest of the present invention laid open and showing the interior thereof.
Figure 4:
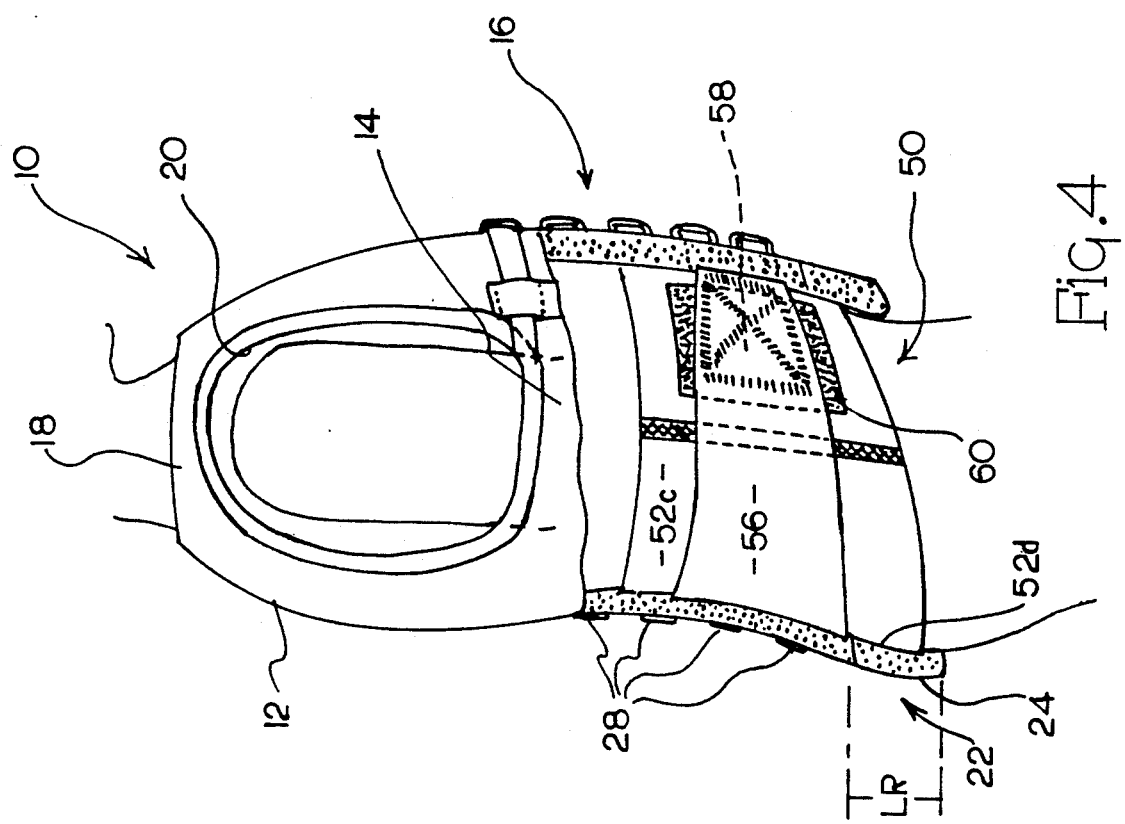
FIG. 4 is a side elevational view similar to FIG. 3 except that a lower portion of the water ski vest is shown in section to better illustrate the internal compression belt that forms a part of the water ski vest.

In order to provide positive lumbar support to a subject wearing the water ski vest 10 of the present invention, a compression belt, indicated generally by the numeral 50, is integrally constructed with the ski vest 10. As indicated in FIG. 2, the compression belt 50 is stitched by a stitch seam 62 to the back panel 12 of the ski vest 10. Note that the compression belt 50 is secured to the inside or to the interior of the ski vest 10 and is disposed about a lower portion of the ski vest, as illustrated in FIGS. 2 and 4.

Turning to a discussion of the compression belt, it is seen that the same includes a main belt 52 that includes opposed ends 52a and 52b. Compression belt 50 includes a central back panel or section 52c that lies directly adjacent the back panel 12 of the ski vest when the ski vest is disposed in the position shown in FIG. 2 and when the ski vest 10 is worn by an individual. Main belt 52 includes a lumbar extension 52d that is designed to extend over and wrap around the lumbar region LR of the individual wearing the ski vest 10. Note that the lumbar extension 52d extends downwardly and forms a part of the central back section 52c of the compression belt. Again, it is stressed that the lumbar extension 52d of the compression belt 50 extends downwardly and wraps around the lumbar region LR of the individual wearing the water ski vest 10.

Continuing to refer to the compression belt 50, it is seen that the same includes mating hook and loop fasteners of the "Velcro ®" type formed on the opposed ends 52a and 52b of the main belt 50. The mating hook and loop fasteners 54 enable the main belt 52 to be pulled tightly around the waist and lumbar region of the person wearing the ski vest 10.

The compression belt 50 further includes a pair of tightener straps 56. Each tightener strap extends from the back central area of the central section 52c around the side of the main belt 52. Formed on the remote ends of the tightener straps 56 are hook and/or loop mating fasteners 58 that are adapted to mate with hook and/or loop fasteners 60 formed on the outside of the main belt 52 just inwardly of the mating hook and loop fasteners 54 disposed on the opposed ends 52a and 52b of the main belt 52. It is appreciated that once the main belt 52 has been fastened around the person wearing ski vest 10, that the tightener straps 56, which are pliable and elastic, are stretched and then secured to the main belt 52. The tightener straps 56, when secured, tend to further tighten and compress the compression belt 50 around the subject wearing the water ski vest 10.

In use, the water ski vest 10 is placed on an individual and the main belt 52 of the compression belt 50 is stretched and extended around the waist and lumbar region LR of the person wearing the ski vest 10. It is appreciated that the entire compression belt in the embodiment illustrated herein is pliable, flexible and elastic. Thus, the opposed ends 52a and 52b of the main belt 52 can be stretched and pulled around the waist of the individual and then fastened by mating hook and loop fasteners 54. To further secure the compression belt 50 around the waist of the individual and around his or her lumbar region LR, the tightener straps 56 are pulled along each side of the main belt 52 and after being stretched and extended, are secured by the cooperating mating hook and loop fasteners 58 and 60. Once the tightener straps 56 are secured around the compression belt 50, it is appreciated that the compression belt 50 compresses around the subject's waist and actually compresses the lumbar region LR of the person wearing the vest and provides positive lumbar support to the person wearing the vest 10. Once the compression belt 50 is securely fastened around the individual, then the front panels 16a and 16b of the vest 10 are closed and the fastener assembly 26 is secured so as to pull and hold the ski vest 10 around that individual.

Figure 3:
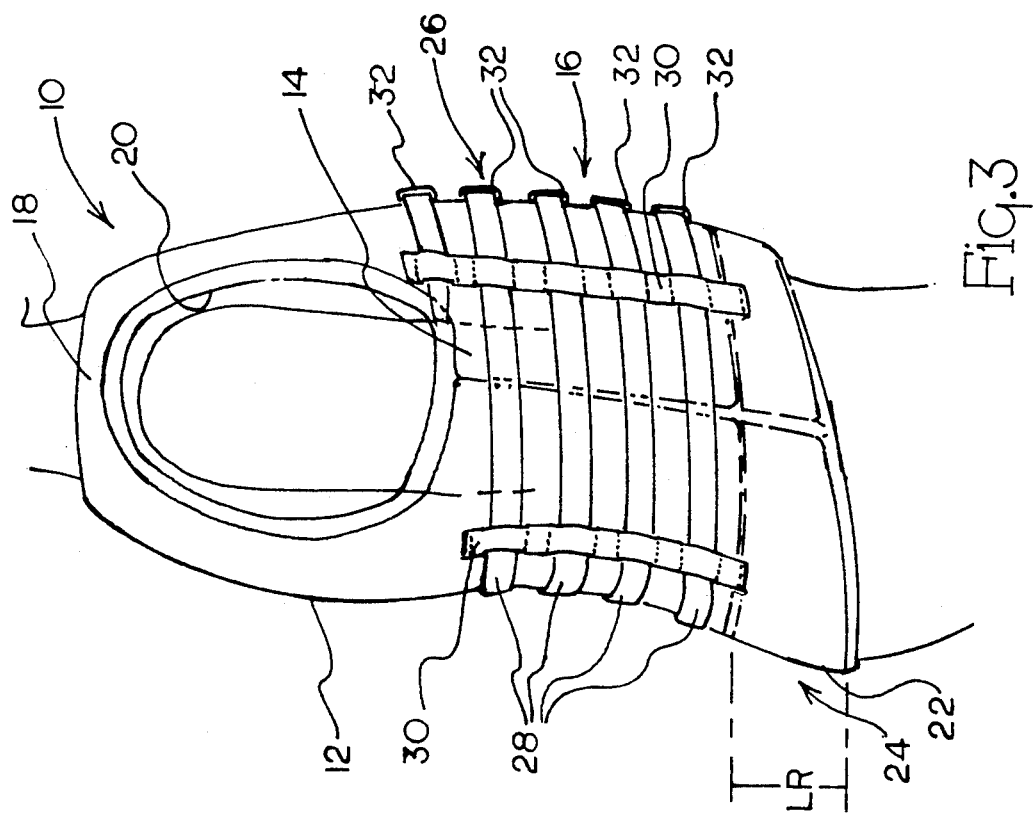
FIG. 3 is a side elevational view of the water ski vest of the present invention secured on an individual.

Note in FIGS. 3 and 4 that with the ski vest 10 and compression belt 50 completely closed around the individual that both the lumbar extension 52 of the ski vest 10 and the lumbar extension 52d of the compression belt both extend downwardly over and wrap around the lumbar region which is referred to by LR. It is appreciated that the lumbar region is that part of the lower back that extends directly above the tail bone, commonly referred to as the sacral, and includes the first five vertebrae that extend immediately above the tail bone. With the compression belt 50 pulled tight and the water ski vest 10 fastened about the individual, it is seen in FIGS. 3 and 4 that a compression action is actually imparted to the lumbar region of the individual wearing the ski vest 10. Compression from the compression belt 50 imparts positive lumbar support to the lumbar region LR of the individual wearing the water ski vest 10.

From the foregoing specification and discussion, it is appreciated that the water ski vest and integral lumbar compression belt of the present invention provide direct and positive lumbar support to an individual wearing the same. Although the present invention has been described in the form of a water ski vest, it is important to appreciate that the present invention would entail any buoyant upper body garment that includes an integral lumbar compression belt. It is important to appreciate that the present design imparts total comfort to an individual and does not have to be custom designed and fitted. Beyond that, the water ski vest 10 of the present invention is easy to use and easy to secure around an individual.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A water ski vest with an inner integral lumbar compression belt for providing positive lumbar support to a subject wearing the water ski vest comprising:
    a) a water ski vest having a back, pair of sides, an openable front, and an exterior and interior surface;
    b) the water ski vest including a lumbar extension extending downwardly from the back and wrapping around the lumbar region of a subject wearing the water ski vest;
    c) an integral compression belt secured to the water ski vest and disposed about the interior surface thereof, the integral compression belt being pliable, elastic and having opposed fastenable end portions; and
    d) the integral compression belt including a lumbar contact portion that extends down and wraps around the lumbar region of the subject when the compression belt assumes a fastened mode such that in a fastened mode the compression belt provides positive lumbar support to the subject wearing the water ski vest and integral lumbar compression belt.

2. The water ski vest and integral lumbar compression belt of claim 1 wherein the compression belt includes a main belt and a pair of side tightener straps that are effective to further tighten the main belt around the subject.

3. The water ski vest and integral compression belt of claim 1 including a stitch structure connecting a central portion of the compression belt to the back of the water ski vest.

4. The water ski vest and integral compression belt of claim 3 wherein the water ski vest includes arm openings and wherein in an expanded open mode the compression belt lies below the arm openings and wherein the opposed ends of the compression belt terminates within the water ski vest when laid out in the open mode.

5. A buoyant upper body garment with an inner integral lumbar compression belt for providing positive lumbar support to a subject comprising:
    a) a buoyant upper body garment having a back, pair of sides, an open front, and an exterior and interior surface;
    b) an integral lumbar compression belt secured to the buoyant upper body garment and disposed about the interior surface thereof, the integral lumbar compression belt being pliable and having fastenable opposed end portions; and
    c) the integral lumbar compression belt including a lumbar contact portion that extends down and wraps around the lumbar region of the subject when the compression belt assumes a fastened mode such that the compression belt provides positive lumbar support to the subject wearing the buoyant upper body garment.

6. The buoyant upper body garment and integral lumbar compression belt of claim 5 wherein the buoyant upper body garment includes a lumbar extension that extends downwardly from the back of the buoyant upper body garment and wraps around the lumbar region of the subject wearing buoyant upper body garment.

7. A method of providing positive lumbar support to a person comprising:
    a) fitting a buoyant garment about the upper body of the person;
    b) connecting a compression belt to the inside of the buoyant garment;
    c) positioning the compression belt with respect to the buoyant garment such that a portion of the compression belt extends downward and wraps around the lumbar region of the person wearing the buoyant garment;
    d) pulling the compression belt tight and fastening the compression belt around the person such that the compression belt engages and compresses against the person and provides positive lumbar support to the person within the buoyant garment; and
    e) fastening the buoyant garment around the compression belt and around the person.

8. A water ski vest with an inner integral compression belt for providing support to a subject wearing the water ski vest comprising:
    a) a water ski vest having a back, a pair of sides, an openable front, and an exterior and interior surface;
    b) an integral compression belt secured to the inside of the water ski vest and including a main section and a pair of fastenable open ends;
    c) means for attaching a portion of the central section of the compression belt to the back of the water ski vest such that a portion of the compression belt and particularly the opposed ends remain free of attachment to the water ski vest; and
    d) the compression belt being flexible, pliable and elastic substantially throughout such that a substantial portion of the compression belt can be stretched with respect to the water ski vest and secured around the subject wearing the water ski vest.

* * * * *